(12) United States Patent
Wang et al.

(10) Patent No.: US 8,513,474 B2
(45) Date of Patent: Aug. 20, 2013

(54) PROCESS FOR THE MANUFACTURE OF FLUORINATED OLEFINS

(75) Inventors: Haiyou Wang, Amherst, NY (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 283 days.

(21) Appl. No.: 12/822,365

(22) Filed: Jun. 24, 2010

(65) Prior Publication Data

US 2011/0319674 A1    Dec. 29, 2011

(51) Int. Cl.
  *C07C 17/00* (2006.01)
  *C07C 17/10* (2006.01)

(52) U.S. Cl.
  USPC .......................... 570/156; 570/155; 570/176

(58) Field of Classification Search
  USPC .......................... 570/156, 155, 176
  See application file for complete search history.

(56) References Cited

U.S. PATENT DOCUMENTS

| | | | |
|---|---|---|---|
| 2,500,920 | A | 3/1950 | Dague et al. |
| 6,239,325 | B1 | 5/2001 | Kishimoto et al. |
| 7,026,520 | B1 | 4/2006 | Mukhopadhyay et al. |
| 7,420,094 | B2 | 9/2008 | Petrov et al. |
| 7,470,828 | B2 | 12/2008 | Nair et al. |
| 7,560,602 | B2 * | 7/2009 | Van Der Puy et al. ........ 570/156 |
| 2005/0124840 | A1 | 6/2005 | Chen et al. |
| 2009/0043138 | A1 | 2/2009 | Rao et al. |
| 2009/0099395 | A1 | 4/2009 | Sakyu et al. |
| 2009/0209791 | A1 | 8/2009 | Van Der Puy et al. |
| 2010/0004492 | A1 | 1/2010 | Nappa et al. |

FOREIGN PATENT DOCUMENTS

| | | |
|---|---|---|
| EP | 2091896 A1 | 8/2009 |
| WO | 2009/035130 A2 | 3/2009 |
| WO | 2008/054782 A1 | 8/2009 |
| WO | WO2009125199 A2 | 10/2009 |
| WO | WO2009125200 A2 | 10/2009 |
| WO | WO2009125201 A2 | 10/2009 |

OTHER PUBLICATIONS

Linyang Bai et al.; Effect of Calcination Atmosphere on the Catalytic Properties of PtSnNaMg/ZSM-5 for Propane Dehydrogenation. Catalysis Communications, Sep. 15, 2009, pp. 2013-2017, vol. 10, Issue 15, Elsevier (publ), US.

* cited by examiner

*Primary Examiner* — Kamal Saeed
*Assistant Examiner* — Janet L Coppins
(74) *Attorney, Agent, or Firm* — Bruce O. Bradford

(57) ABSTRACT

Provided are methods for producing fluorinated organic compounds, which preferably comprises converting at least one compound of formula (I) $CH_2XCHZCF_3$ to at least one compound of formula (II) $CHX=CZCF_3$ where X and Z are independently H or F, with the proviso that X and Z are not the same. The converting step comprises catalytically reacting at least one compound of formula (I), preferably via dehydrogenation or oxidative dehydrogenation. In another aspect, the inventive method of preparing fluorinated organic compounds comprises converting a reaction stream comprising at least one pentafluoropropene to a product stream comprising at least one pentafluoropropane and at least one compound of formula (I), separating out the compound of formula (I) from the product stream, and converting the compound of formula (I) separated from the product stream to at least one compound of formula (II), wherein the conversion the compound of formula (I) to 3,3,3-trifluoropropyne is substantially limited.

15 Claims, No Drawings

PROCESS FOR THE MANUFACTURE OF FLUORINATED OLEFINS

BACKGROUND OF THE INVENTION

1. Field of Invention

The present invention relates to novel methods of preparing fluorinated organic compounds, and particularly to methods of producing fluorinated olefins.

2. Description of Related Art

Hydrofluorocarbons ("HFCs"), in particular hydrofluoroolefins ("HFOs") such as tetrafluoropropenes (including 2,3,3-tetrafluoropropene ("HFO-1234yf") and 1,3,3,3-tetrafluoropropene ("HFO-1234ze")) have been disclosed to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons ("CFCs") and hydrochlorofluorocarbons ("HCFCs"), both of which potentially damage the Earth's ozone layer, HFCs do not contain chlorine and thus pose no threat to the ozone layer.

Several methods for preparing fluorinated olefins from fluorinated alkanes are known. For example, U.S. Pat. No. 7,560,602 discloses that $CF_3CF=CHF$ ("HFO-1225ye") and HFO-1234yf can be produced via gas phase dehydrofluorination of $CF_3CHFCHF_2$ and $CF_3CHFCH_2F$, respectively, over a dehydrofluorination catalyst selected from the group consisting of one or more fluorinated metal oxides, metal fluorides, carbon supported transition metals and combinations of these. U.S. Publication No. 2009/0099395 discloses that HFO-1234ze may be produced via gas phase dehydrofluorination of $CF_3CH_2CHF_2$ by a catalytic process using a zirconium compound-carried catalyst. U.S. Publication No. 2009/0043138 discloses that HFO-1234ze and $CF_3CH=CF_2$ ("HFO-1225zc") may be produced from the dehydrofluorination of $CF_3CH_2CHF_2$ and $CF_3CH_2CF_3$ using oxides, fluorides, and oxyfluorides of magnesium, zinc, and mixtures of magnesium and zinc.

Methods for dehydrogenating alkanes into alkenes are known. One such method utilizes mixed metal oxides as dehydrogenation catalysts. For example, U.S. Pat. No. 2,500,920 discloses that chromium oxide catalysts on an alumina support can catalyze dehydrogenation of an alkane to an alkene. Similarly, mixed metal oxide catalysts having Mo—Sb—W or Cr—Sb—W, and at least one metal selected from the group consisting of V, Nb, K, Mg, Sn, Fe, Co, and Ni, can drive oxidative dehydrogenation of propane to propene, as disclosed by U.S. Pat. No. 6,239,325.

Applicants have come to recognize, however, that the above-mentioned mixed metal oxides are not suitable for use in the dehydrogenation of hydrofluorocarbons because of their tendency to react with hydrofluorocarbons, causing the conversion of metal oxides into metal oxyfluorides or even metal fluorides, and the collapse of catalyst structure.

Applicants have also come to recognize that there are significant deficiencies associated with the above-referenced methods, and that such methods are not suitable for producing HFOs such as HFO-1234yf and HFO-1234ze from certain fluorinated alkanes and alkenes. For example, Applicants have found that the dehydrofluorination of 2,3,3,3-tetrafluoropropane ("HFO-254eb") and 1,3,3,3-tetrafluoropropane ("HFO-254fb") in the presence of these catalysts forms the byproduct 3,3,3-trifluoropropyne, the toxicity of which is unknown.

Accordingly, Applicants have come to recognize that a need exists for a method of preparing HFOs from fluorinated alkanes, particularly for preparing HFO-1234yf and HFO-1234ze from HFC-254eb and HFC-254fb, whereby the formation of 3,3,3-trifluoropropyne is substantially limited. This invention satisfies this need among others.

SUMMARY OF THE INVENTION

In one aspect of the present invention, applicants have developed methods for producing fluorinated organic compounds, including HFOs in general and tetrafluoropropenes in particular embodiments, which preferably comprise converting at least one compound of formula (I):

$$CH_2XCHZCF_3 \quad\quad (I)$$

to at least one compound of formula (II):

$$CHX=CZCF_3 \quad\quad (II)$$

where X and Z are independently H or F, with the proviso that X and Z are not the same.

In certain embodiments the converting step of the present invention comprises catalytically reacting at least one compound of formula (I), preferably via dehydrogenation or oxidative dehydrogenation. The catalytic reaction step preferably comprises exposing at least one compound of formula (I) to a dehydrogenation catalyst or combination of dehydrogenation catalysts, preferably comprising one or more Group VIII noble metals supported on a metal oxyfluoride support. In certain preferred embodiments, the converting step further comprises exposing at least one compound of formula (I) to one or more oxidants, preferably selected from the group consisting of $O_2$, $CO_2$, $N_2O$, and mixtures thereof.

In another aspect, the present invention is directed to a method of preparing fluorinated organic compounds comprising converting a reaction stream comprising at least one pentafluoropropene to a product stream comprising a mixture of at least one pentafluoropropane and a compound of formula (I), separating out at least a portion of the compound of formula (I) from the product stream, and converting the compound of formula (I) separated from the product stream to at least one compound of formula (II). In a preferred embodiment, the method further comprises substantially minimizing, and preferably substantially avoiding, the conversion of said compound of formula (I) to 3,3,3-trifluoropropyne.

DETAILED DESCRIPTION OF PREFERRED EMBODIMENTS

One aspect of the present invention relates to methods for producing HFOs from hydrofluorocarbons having at least two hydrogens on adjacent carbons via dehydrogenation or oxidative dehydrogenation. In one preferred aspect, the present invention relates to the conversion of tetrafluoropropane to tetrafluoropropene via catalytic dehydrogenation or catalytic oxidative dehydrogenation. The methods of the present invention preferably comprise converting a compound of formula (I) to an HFO, preferably a C3 HFO, more preferably a compound of formula (II). In highly preferred embodiments the present invention comprises converting HFC-254eb and/or HFC-254fb to HFO-1234yf and/or HFO-1234ze.

Conversion of Compounds of Formula (I)

One beneficial aspect of the present invention is that it enables the conversion of hydrofluorocarbons, such as compounds of formula (I), to HFOs, such as compounds of formula (II), with the ability to achieve relatively high conversion and high selectivity reactions. The preferred converting step of the present invention is carried out under conditions effective to convert, and preferably convert at least about 15%, more preferably at least about 30%, even more preferably at least about 50%, and even more preferably about 90% of said compound of formula (I). It is also generally preferred that the converting step produces a reaction product having at least about 50% selectivity, more preferably at least about 70% selectivity, and even more preferably at least about 90% selectivity, to compounds of formula (II). In certain highly preferred embodiments the selectivity to tetrafluoropropene is at least about 95%.

The converting step can be carried out in the liquid phase or in the gas phase, or in a combination of gas and liquid phases, and it is contemplated that the reaction can be carried out batch wise, continuous, or a combination of these. Preferably, in certain embodiments, the reaction is carried out as a gas phase reaction. It is contemplated that the converting step can be carried out in any suitable reaction vessel or reactor, which may be single or multiple tubes. In preferred embodiments the converting step is carried out in a fixed-bed reactor.

The gas phase reaction may be conducted, for example, by introducing a gaseous form of a compound of formula (I), and preferably HFC-254eb, HFC-254fb, and mixtures thereof, into a suitable reaction vessel or reactor. Preferably, the vessel is comprised of materials which are resistant to corrosion, such as Hastelloy, Inconel, Monel, and/or stainless steel. In preferred embodiments, the vessel contains a catalyst, preferably a dehydrogenation or oxidative dehydrogenation catalyst, and is fitted with suitable means to heat the reaction mixture to the desired reaction temperature.

In a preferred embodiment, at least one compound of formula (I) is introduced into a reactor either in pure form, impure form, or together with an optional inert gas diluent, such as nitrogen, argon, and so on, as is readily apparent to one skilled in the art. Preferably, at least one compound of formula (I) is pre-vaporized or preheated prior to entering the reactor. Alternatively, compounds of formula (I) may be vaporized inside of the reactor.

Catalytic Dehydrogenation

In one aspect of the present invention, the converting step is carried out via dehydrogenation in which at least one compound of formula (I) is exposed to a dehydrogenation catalyst or combination of dehydrogenation catalysts. Preferably, a feed stream comprising the compound of formula (I), optionally together with a stream of hydrogen, is fed into a dehydrogenation reactor charged with the dehydrogenation catalyst under conditions effective to produce a product stream comprising at least one compound of formula (II).

Preferably, the dehydrogenation catalyst comprises one or more Group VIII noble metals supported on a metal oxyfluoride support, or one or more metal oxyfluoride catalysts. Non-limiting examples of Group VIII noble metals include Pt, Rh, Ru, Pd, Ir, and so forth, as are apparent to one of ordinary skill in the art. Non-limiting examples of useful supports include oxyfluorides of Zr, Al, Ga, Cr, La, Ti, Fe, Mg, and mixtures thereof. Non-limiting examples of metal oxyfluoride catalysts include oxyfluorides of Ni, Co, Mg, Al, Ga, Cr, La, Y, Fe, Zr, and mixtures thereof. It is expected that many other catalysts may be used depending on the requirements of particular embodiments in view of the teachings contained herein. Of course, two or more of these catalysts, or other catalysts not named here, may be used in combination.

While it is contemplated that a wide variety of reaction temperatures may be used, depending on relevant factors such as the catalyst being used and the most desired reaction product, it is generally preferred that the reaction temperature is from about 400° C. to about 800° C. Preferred reaction temperatures may range from about 500° C. to about 700° C., and more preferably from about 550° C. to about 650° C.

In general, it is also contemplated that a wide variety of reaction pressures may be used, depending again on relevant factors such as the specific catalyst being used and the most desired reaction product. The reaction pressure can be, for example, super-atmospheric, atmospheric, or under vacuum, and in certain preferred embodiments is from about 0.1 to about 5 atm.

Catalytic Oxidative Dehydrogenation

In one aspect of the present invention, the converting step is carried out via oxidative dehydrogenation in which at least one compound of formula (I) is exposed to an oxidative dehydrogenation catalyst or combination of oxidative dehydrogenation catalysts. Preferably, a feed stream comprising the compound of formula (I) together with a stream of pure or diluted oxidant, is fed into a dehydrogenation reactor containing the oxidative dehydrogenation catalyst under conditions effective to produce a product stream comprising at least one compound of formula (II).

Preferably, the oxidative dehydrogenation catalyst comprises one or more Group VIII noble metals supported on a metal oxyfluoride support, or one or more metal oxyfluoride catalysts. Non-limiting examples of such catalysts are described above, and are apparent to one of ordinary skill in the art. Non-limiting examples of oxidants include $O_2$, $CO_2$, and $N_2O$, and so forth, as are apparent to one of ordinary skill in the art. It is expected that many other catalysts may be used depending on the requirements of particular embodiments in view of the teachings contained herein. Of course, two or more of these catalysts, or other catalysts not named here, may be used in combination.

While it is contemplated that a wide variety of reaction temperatures may be used in catalytic oxidative dehydrogenation, depending on relevant factors such as the catalyst being used and the most desired reaction product, it is generally preferred that the reaction temperature is from about 300° C. to about 700° C. Preferred reaction temperatures may range from about 400° C. to about 600° C., and more preferably from about 450° C. to about 550° C.

Regeneration of Catalyst

In both catalytic dehydrogenation and catalytic oxidative dehydrogenation, it is contemplated that the amount of catalyst used will vary depending on the particular parameters present in each. It is also contemplated that after use for a period of time in the converting step, the activity of the catalyst may decrease. When this occurs, the catalyst may be regenerated. Although it is contemplated that regeneration of the catalyst may be accomplished by any means known in the art, the catalyst is preferably regenerated by passing air or oxygen diluted with nitrogen over the catalyst at temperatures of from about 200° C. to about 600° C., preferably from about 350° C. to about 450° C., for from about 0.5 hours to about three days, optionally followed by either (1) treatment with HF at temperatures of from about 100° C. to about 400° C., preferably of from about 200° C. to about 350° C., for metal oxyfluoride catalysts, or (2) treatment with $H_2$ at temperatures of from about 100° C. to about 400° C., preferably of from about 200° C. to about 350° C., for Group VIII noble metal catalysts.

Conversion of Pentafluoropropenes to Compounds of Formula (II) while Substantially Limiting the Production of 3,3,3-Trifluoropropyne The present invention involves in one aspect methods for converting pentafluoropropenes to at least one compound of formula (II) comprising: (a) converting at least one pentafluoropropene, preferably CF$_3$CF=CHF ("HFO-1225ye"), in the presence of a hydrogenation catalyst to a first reaction product comprising at least one pentafluoropropane, preferably CF$_3$CHFCH$_2$F ("HFC-245eb"); and (b) converting said at least one pentafluoropropane in the presence of a dehydrofluorination catalyst to at least one compound of formula (II). Applicants have found that said first reaction product comprises compounds of formula (I) that are generated in step (a) through the hydrodefluorination of said pentafluoropropanes. Applicants have further come to recognize that notable amounts of 3,3,3-trifluoropropyne are formed as a byproduct in step (b) through the dehydrofluorination of the at least one compound of formula (I), thereby reducing selectivity for compounds of formula (II). Accordingly, one aspect of the present invention is directed to methods of converting pentafluoropropenes, preferably HFO-1225ye, to compounds of formula (II) wherein the production of 3,3,3-trifluoropropyne is substantially limited.

In preferred embodiments, the inventive method comprises processing a first reaction stream comprising pentafluoropropene, preferably HFO-1225ye, to a final product stream comprising at least one compound of formula (II), wherein said conditions are effective to substantially limit the concentration of 3,3,3-trifluoropropyne present in said final product stream. Preferably, the concentration of said 3,3,3-trifluoropropyne in said final product stream is substantially limited to a concentration of less than about 100 parts per million, preferably less than about 50 parts per million, and even more preferably less than about 20 parts per million.

In certain preferred embodiments, said processing step comprises the steps of: (a) catalytically hydrogenating said pentafluoropropene in said first reaction stream to obtain a first intermediate stream comprising pentafluoropropane, preferably HFC-245eb, and at least one compound of formula (I); and (b) separating said at least one compound of formula (I) from said first intermediate stream to obtain a separated intermediate stream and a second intermediate stream, wherein said separated intermediate stream comprises a higher concentration of said at least one compound of formula (I) than said second intermediate stream. In certain preferred embodiments, the method further comprises the steps of: (c) dehydrofluorinating said second intermediate stream under conditions effective to produce at least one compound of formula (II); and/or (d) converting said separated intermediate stream under conditions effective to produce said final product stream comprising at least one compound of formula (II).

Preferably, said catalytic hydrogenation step (a) comprises exposing said pentafluoropropene to a supported hydrogenation catalyst in the presence of hydrogen, wherein said supported hydrogenation catalyst preferably comprises a zero-valent metal disposed on a support comprising alpha-alumina. Preferably, said separation step (b) comprises removing at least a portion, preferably at least about 50%, and even more preferably at least about 90% of said at least one compound of formula (I) from said first intermediate stream, preferably by distillation. In certain preferred embodiments, the distillation step is conducted in a standard distillation column at atmospheric pressure, super-atmospheric pressure, or a vacuum. Preferably, the pressure is less than about 300 psig, more preferably less than about 150 psig, and even more preferably less than 100 psig. Suitable distillation operating temperatures can be selected in view of the teachings contained herein and in view of thither operating conditions, such as the pressure of the distillation column. Further examples of such separation methods will be apparent to one skilled in the art. Preferably, said dehydrofluorination step (c) comprises reacting said second intermediate stream with a strong caustic solution or in the presence of a dehydrofluorination catalyst. In preferred embodiments, the second intermediate stream is reacted in a caustic solution comprising KOH, NaOH, Ca(OH)$_2$, and CaO at an elevated temperature in a liquid phase reactor. In other preferred embodiments, the second intermediate stream is reacted in the presence of a dehydrofluorination catalyst comprising fluorinated Cr$_2$O$_3$, fluorinated Al$_2$O$_3$, and/or AlF$_3$ at an elevated temperature in a gas phase reactor. Preferably, said converting step (d) comprises catalytic dehydrogenation or catalytic oxidative dehydrogenation, as is described in detail above.

EXAMPLES

The following examples are provided for the purpose of illustrating the present invention, but without limiting the scope thereof.

Example 1

This example illustrates the catalytic dehydrogenation of HFC-254eb. A stainless steel tube reactor (0.75" O.D.×0.625" I.D.×23.0" L) was charged with 20 cc of 0.5 weight % Pt/AlO$_{0.75}$F$_{150}$ catalyst pellets. The reactor was heated by a 12" split tube furnace. A multi-point thermocouple, inserted through the catalyst bed, was used to measure the temperatures of catalyst bed. The operating conditions of a typical run included a H$_2$ to HFC-254eb mole ratio of 0.25, a contact time of 30 seconds, at atmospheric pressure, and a reaction temperature of 600° C. The effluent was analyzed by an on-line GC to determine the HFC-254eb conversion rate and the HFO-1234yf selectivity. After 2 hours of reaction, the HFC-254eb conversion rate and HFO-1234yf selectivity were determined to be 31% and 94%, respectively.

Example 2

This example illustrates the catalytic oxidative dehydrogenation of HFC-254eb. A stainless steel tube reactor (0.75" O.D.×0.625" I.D.×23.0" L) was charged with 20 cc of 25 weight % MgO$_{0.33}$F$_{1.33}$—75 weight % of AlO$_{0.75}$F$_{150}$ catalyst pellets. The reactor was heated by a 12" split tube furnace. A multi-point thermocouple, inserted through the catalyst bed, was used to measure the temperatures of catalyst bed and at the top of the catalyst bed. The operating conditions of a typical run included an O$_2$ to HFC-254eb mole ratio of 0.5, a contact time of 30 seconds, at atmospheric pressure, and a reaction temperature of 500° C. The effluent was analyzed by an on-line GC to determine the HFC-254eb conversion rate and the HFO-1234yf selectivity. After 2 hours of reaction, the HFC-254eb conversion rate and HFO-1234yf selectivity were determined to be 15% and 51%, respectively.

What is claimed is:

1. A method of preparing fluorinated organic compounds comprising converting via dehydrogenation at least one compound of formula (I):

$$CH_2XCHZCF_3 \tag{I}$$

to at least one compound of formula (II):

$$CHX=CZCF_3 \tag{II}$$

where X and Z are each independently H or F, with the proviso that X and Z are not the same.

2. The method of claim 1 wherein said compound of formula (I) comprises HFC-254eb and said compound of formula (II) comprises HFO-1234yf.

3. The method of claim 1 wherein said compound of formula (I) comprises HFC-254fb and said compound of formula (II) comprises HFO-1234ze.

4. The method of claim 1 wherein said converting step is carried out under conditions effective to convert at least about 15% of said compound of formula (I) and to provide a selectivity to said compound of formula (II) of at least about 50%.

5. The method of claim 1 wherein said converting step is carried out under conditions effective to convert at least about 30% of said compound of formula (I) and to provide a selectivity to said compound of formula (II) of at least about 90%.

6. The method of claim 1 wherein said converting step comprises exposing said compound of formula (I) to a dehydrogenation catalyst or combination of dehydrogenation catalysts.

7. The method of claim 6 wherein said dehydrogenation catalyst comprises one or more Group VIII noble metals supported on a metal oxyfluoride support.

8. The method of 7 wherein said one or more Group VIII noble metals is selected from the group consisting of Pt, Rh, Ru, Pd, and mixtures thereof.

9. The method of claim 7 wherein said metal oxyfluoride support is selected from the group consisting of oxyfluorides of Zr, Al, Ga, Cr, La, Y, Fe, Mg, and mixtures thereof.

10. The method of claim 6 wherein said dehydrogenation catalyst comprises a metal oxyfluoride catalyst.

11. The method of claim 10 wherein said metal oxyfluoride catalyst is selected from the group consisting of oxyfluorides of Ni, Co, Mg, Al, Ga, Cr, La, Y, Fe, Zr, and mixtures thereof.

12. The method of claim 6 wherein said converting step further comprises exposing said compound of formula (I) to one or more oxidants.

13. The method of claim 12 wherein said one or more oxidants is selected from the group consisting of $O_2$, $CO_2$, $N_2O$, and mixtures thereof.

14. The method of claim 6 wherein said converting step comprises conducting at least a portion of said converting step in the gas phase at a temperature of from about 400° C. to about 800° C. and at a pressure of from about 0.1 to about 5.0 atm.

15. The method of claim 12 wherein said converting step comprises conducting at least a portion of said converting step in the gas phase at a temperature of from about 300° C. to about 700° C.

* * * * *